US012749245B2

(12) United States Patent
Chen et al.

(10) Patent No.: US 12,749,245 B2
(45) Date of Patent: Sep. 29, 2026

(54) IMAGING METHOD FOR STATIC CT APPARATUS, STATIC CT APPARATUS, ELECTRONIC DEVICE, AND MEDIUM

(71) Applicants: NUCTECH COMPANY LIMITED, Beijing (CN); TSINGHUA UNIVERSITY, Beijing (CN)

(72) Inventors: Zhiqiang Chen, Beijing (CN); Li Zhang, Beijing (CN); Hu Tang, Beijing (CN); Yunda Sun, Beijing (CN); Xin Jin, Beijing (CN); Zhenhua Zhao, Beijing (CN); Le Shen, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 159 days.

(21) Appl. No.: 18/570,387

(22) PCT Filed: Aug. 31, 2023

(86) PCT No.: PCT/CN2023/116137
§ 371 (c)(1),
(2) Date: Dec. 14, 2023

(87) PCT Pub. No.: WO2024/046424
PCT Pub. Date: Mar. 7, 2024

(65) Prior Publication Data
US 2025/0095240 A1 Mar. 20, 2025

(30) Foreign Application Priority Data
Aug. 31, 2022 (CN) ......................... 202211059887.2
Jul. 26, 2023 (WO) ................ PCT/CN2023/109310

(51) Int. Cl.
*G06T 12/20* (2026.01)
*A61B 6/00* (2024.01)
(Continued)

(52) U.S. Cl.
CPC ............ *G06T 12/20* (2026.01); *A61B 6/5241* (2013.01); *G06T 5/50* (2013.01); *G06T 7/11* (2017.01);
(Continued)

(58) Field of Classification Search
CPC ........ G06T 11/005; G06T 11/006; G06T 7/11; G06T 5/50; G06T 2207/10081;
(Continued)

(56) References Cited

U.S. PATENT DOCUMENTS 12,067,651 B2 * 8/2024 Tang ........................ G06N 3/08
2008/0056435 A1 * 3/2008 Basu ...................... A61B 6/027
378/9
(Continued)

FOREIGN PATENT DOCUMENTS

CN 103473745 A 12/2013
CN 108577876 A 9/2018
(Continued)

OTHER PUBLICATIONS

International Search Report and Written Opinion for PCT application No. PCT/CN2023/116137 dated Nov. 15, 2023 (6 pages).
(Continued)

*Primary Examiner* — John Villecco
(74) *Attorney, Agent, or Firm* — Merchant & Gould P.C.

(57) ABSTRACT

A static CT apparatus and an imaging method for the same are provided. The imaging method includes: acquiring initial projection data of an inspected object at different angles by using a distributed ray source and a detector, where the initial projection data includes projection data that is directly obtained by the detector based on the rays emitted from a plurality of ray source points; obtaining a first CT image using a reconstruction algorithm according to the acquired initial projection data; dividing the first CT image into N first
(Continued)

sub-images, where N is a positive integer greater than or equal to 1, and a union of the N first sub-images covers the entire first CT image; optimizing the N first sub-images to obtain N second sub-images; and merging the N second sub-images to obtain a second CT image.

26 Claims, 11 Drawing Sheets

(51) Int. Cl.
*G06T 5/50* (2006.01)
*G06T 7/11* (2017.01)

(52) U.S. Cl.
CPC ............... *G06T 2207/10081* (2013.01); *G06T 2207/20081* (2013.01); *G06T 2207/20084* (2013.01); *G06T 2207/20221* (2013.01)

(58) Field of Classification Search
CPC ......... G06T 2211/408; G06T 2211/424; G06T 2211/436; G06T 2211/441; G06T 5/60; A61B 6/5241; A61B 6/03; A61B 6/032; A61B 6/482; A61B 6/4014
See application file for complete search history.

(56) References Cited

U.S. PATENT DOCUMENTS

| | | | | |
|---|---|---|---|---|
| 2016/0048972 | A1* | 2/2016 | Kam | G06T 7/0016 382/128 |
| 2017/0061654 | A1* | 3/2017 | Litvin | G06T 11/008 |
| 2017/0161923 | A1* | 6/2017 | Nakano | G06T 3/4007 |
| 2018/0286087 | A1 | 10/2018 | Ray et al. | |
| 2019/0057488 | A1* | 2/2019 | Li | G06T 7/136 |
| 2019/0206095 | A1* | 7/2019 | Xing | G06T 11/003 |
| 2020/0043204 | A1 | 2/2020 | Fu et al. | |
| 2020/0184639 | A1* | 6/2020 | Park | G06T 11/003 |
| 2020/0390414 | A1* | 12/2020 | Ikhlef | G06N 3/094 |
| 2021/0007695 | A1 | 1/2021 | Lu et al. | |
| 2021/0123999 | A1* | 4/2021 | An | G01R 33/56308 |
| 2023/0011759 | A1* | 1/2023 | Lu | G06T 5/20 |
| 2023/0081601 | A1* | 3/2023 | Wang | A61B 6/488 378/96 |
| 2023/0083935 | A1* | 3/2023 | Lu | A61B 6/032 382/131 |
| 2024/0104705 | A1* | 3/2024 | Zhao | G06T 7/11 |
| 2024/0212163 | A1* | 6/2024 | Yang | G06T 11/008 |
| 2024/0355094 | A1* | 10/2024 | Kastryulin | G06V 10/235 |
| 2025/0005818 | A1* | 1/2025 | Lu | G06T 11/006 |

FOREIGN PATENT DOCUMENTS

| | | | |
|---|---|---|---|
| CN | 109658464 | A | 4/2019 |
| CN | 110599420 | A | 12/2019 |
| CN | 111265231 | A | 6/2020 |
| CN | 112424835 | A | 2/2021 |
| CN | 113269846 | A | 8/2021 |
| CN | 114199907 | A | 3/2022 |
| JP | 2014195526 | A | 10/2014 |
| KR | 10-2022-0117478 | * | 8/2024 |
| WO | 2019060843 | A1 | 3/2019 |

OTHER PUBLICATIONS

International Search Report and Written Opinion for PCT application No. PCT/CN2023/109310 dated Sep. 7, 2023 (7 pages).
Extended European Search Report dated Jun. 9, 2026 for corresponding EP Application No. 23825176.3 (3 pgs).
Office Action dated Aug. 21, 2026 for corresponding Chinese Application No. 202311115401.7 (18 pages including English Translation).

* cited by examiner

IMAGING METHOD FOR STATIC CT APPARATUS, STATIC CT APPARATUS, ELECTRONIC DEVICE, AND MEDIUM

CROSS-REFERENCE TO RELATED APPLICATIONS

This application is a National Stage Application of International Application No. PCT/CN2023/116137, filed on Aug. 31, 2023, which claims benefit of Ser. No. 202211059887.2, filed on Aug. 31, 2022 in China and International Application No. PCT/CN2023/109310, filed on Jul. 26, 2023, and which applications are incorporated herein by reference. To the extent appropriate, a claim of priority is made to each of the above disclosed applications.

TECHNICAL FIELD

The present disclosure relates to fields of image processing, radiation inspection imaging and security inspection technologies, and in particular to an imaging method for a static CT apparatus, a static CT apparatus, an electronic device, a computer-readable storage medium, and a program product.

BACKGROUND

With a gradual maturity of a distributed ray source technology, a static CT apparatus with a distributed ray source has gradually entered fields such as security inspection and medical care. In a traditional slip ring CT apparatus, a ray source with a single ray source point may be used for imaging as a slip ring rotates. In a static CT apparatus with a distributed ray source, the distributed ray source is arranged around an apparatus channel, and ray scanning at different angles may be completed through a rapid switching of ray source points. Beam outputs of the distributed ray source may be separately controlled, so as to achieve scanning in an arbitrary triggering sequence, and a scanning mode is more flexible. However, due to limitations in size requirements for the distributed ray source and the apparatus, an optical path arrangement of the static CT apparatus may not necessarily be a regular ring-shaped arrangement. Due to differences in the arrangement and the beam output mode, an image reconstruction method used in the traditional slip ring CT apparatus is not applicable to the static CT apparatus.

The above information disclosed in this section is just for understanding of a background of an inventive concept of the present disclosure. Therefore, the above information may contain information that does not constitute a related art.

SUMMARY

In view of at least one aspect of the aforementioned technical problems, an imaging method for a static CT apparatus, a static CT apparatus, an electronic device, a computer-readable storage medium, and a program product are proposed.

In an aspect, an imaging method for a static CT apparatus is provided. The static CT apparatus includes a distributed ray source and a detector, the distributed ray source includes a plurality of ray source points configured to emit rays towards an inspected object, and the detector includes a plurality of detector units configured to detect the rays passing through the inspected object. The imaging method includes: an initial projection data acquisition step of acquiring initial projection data of the inspected object at different angles by using the distributed ray source and the detector, where the initial projection data includes projection data that is directly obtained by the detector based on the rays emitted from the plurality of ray source points; a first image reconstruction step of obtaining a first CT image using a reconstruction algorithm according to the acquired initial projection data; an image segmentation step of dividing the first CT image into N first sub-images, where N is a positive integer greater than or equal to 1, and a union of the N first sub-images covers the entire first CT image; a first optimization step of optimizing the N first sub-images to obtain N second sub-images; and an image merging step of merging the N second sub-images to obtain a second CT image.

According to some embodiments, the plurality of ray source points include a first-type ray source point and a second-type ray source point, and the first-type ray source point is at least one of the plurality of ray source points; the initial projection data includes first projection data and second projection data, the first projection data is projection data directly obtained based on a ray emitted from the first-type ray source point, and the second projection data is projection data directly obtained based on a ray emitted from the second-type ray source point; and the N first sub-images are optimized with the first projection data as an optimization objective in a process of optimizing the N first sub-images.

According to some embodiments, a frequency of the ray emitted from the first-type ray source point is higher than a frequency of the ray emitted from the second-type ray source point.

According to some embodiments, in the first optimization step, the N first sub-images are optimized using a first neural network model to obtain the N second sub-images, and the first neural network model is pre-trained.

According to some embodiments, the first neural network model is pre-trained by: performing a forward projection on each second sub-image according to the first-type ray source point so as to obtain first forward projection data; determining a difference between the first forward projection data and the first projection data; and adjusting a parameter of the first neural network model according to the difference between the first forward projection data and the first projection data, so as to minimize the difference between the first forward projection data and the first projection data.

According to some embodiments, the plurality of ray source points includes K first-type ray source points, where K is a positive integer greater than or equal to 1; and the initial projection data includes K first projection data $R_j$, the first projection data $R_j$ is projection data directly obtained based on a ray emitted from a $j^{th}$ first-type ray source point, j is a positive integer, and $1 \le j \le K$.

According to some embodiments, the dividing the first CT image into N first sub-images includes: performing a forward projection on the first CT image Q according to the K first-type ray source points so as to obtain K first initial projection data $P_j$, where the first initial projection data $P_j$ is projection data obtained by performing a forward projection on the first CT image Q according to the $j^{th}$ first-type ray source point; and performing a forward projection on each first sub-image $Q_i$ according to the K first-type ray source points so as to obtain K first projection sub-data $P_{i,j}$, where the first projection sub-data $P_{i,j}$ is projection data obtained by performing a forward projection on an $i^{th}$ first sub-image $Q_i$ according to the $j^{th}$ first-type ray source point, i is a positive integer, and $1 \le i \le N$, where in a process of dividing the first CT image into N first sub-images, for any first sub-image and any first-type ray source point, the first initial projection data $P_i$ and the first projection sub-data $P_{i,j}$ are consistent in a partial region $U_{i,j}$.

According to some embodiments, the adjusting a parameter of the first neural network model according to the difference between the first forward projection data and the first projection data so as to minimize the difference between the first forward projection data and the first projection data includes:

for each first sub-image $Q_i$, using a first optimization objective function to minimize the difference between the first forward projection data and the first projection data, where the first optimization objective function is $$\min_{Q} \operatorname{sum}_{j} \left(dis\left(R_j, \overline{P_{i,j}}: U_{i,j}\right)\right),$$

and j takes values from 1 to K sequentially.

In the first optimization objection function, $\overline{Q}_i$ represents an output image of the first neural network model when the first sub-image $Q_i$ is input, $\overline{P_{i,j}}$ represents the first forward projection data, $\overline{P_{i,j}}$ represents the projection data obtained by performing a forward projection on the $i^{th}$ second sub-image $\overline{Q_i}$ according to the $j^{th}$ first-type ray source point, and $dis(R_j, \overline{P_{i,j}}: U_{i,j})$ is a metric function for measuring a distance between $R_j$ and $\overline{P_{i,j}}$ in the region $U_{i,j}$.

According to some embodiments, the adjusting a parameter of the first neural network model according to the difference between the first forward projection data and the first projection data so as to minimize the difference between the first forward projection data and the first projection data includes:

for each first sub-image $Q_i$, using a second optimization objective function to minimize the difference between the first forward projection data and the first projection data, where the second optimization objective function is $$\min \operatorname{sum}_{i} \left(f(\overline{Q}_i)\right),$$

where $$f(\overline{Q}_i) = \operatorname{sum}_{j} \left(dis\left(R_j, \overline{P_{i,j}}: U_{i,j}\right)\right),$$

and i takes values from i to N sequentially.

According to some embodiments, a same metric function is used for each first-type ray source point; or different metric functions are used for at least two of the K first-type ray source points.

According to some embodiments, the metric function includes at least one of an L1-norm distance and an L2-norm distance.

According to some embodiments, the acquiring initial projection data of the inspected object at different angles by using the distributed ray source and the detector includes: acquiring the initial projection data of the inspected object in a predetermined scanning angle range by using the distributed ray source and the detector.

According to some embodiments, the imaging method further includes: a forward projection step of performing a forward projection on the second CT image to obtain second forward projection data; and a second optimization step of processing the second forward projection data to obtain optimized projection data.

According to some embodiments, in the second optimization step, the second forward projection data is processed using a second neural network model to obtain the optimized projection data, and the second neural network model is pre-trained.

According to some embodiments, the second forward projection data includes forward projection data obtained by directly performing a forward projection on the second CT image.

According to some embodiments, the imaging method further includes: a second image reconstruction step of obtaining a third CT image using a reconstruction algorithm based on the optimized projection data.

According to some embodiments, the imaging method further includes: determining the obtained third CT image as the first CT image; and iteratively executing the image segmentation step, the first optimization step, the image merging step, the forward projection step, the second optimization step and the second image reconstruction step until an iteration termination condition is met, and determining the third CT image obtained by a last execution of the second image reconstruction step as a final CT image.

According to some embodiments, the iteration termination condition includes: a number of iterations reaching a specified number of iterations; or a difference between third CT images obtained in two adjacent iterations being less than a specified threshold.

In another aspect, a static CT apparatus is provided, including: a distributed ray source, where the distributed ray source includes a plurality of ray source points configured to emit rays towards an inspected object; a detector, where the detector includes a plurality of detector units configured to detect the rays passing through the inspected object; and an imaging device configured to perform: an initial projection data acquisition step of acquiring initial projection data of the inspected object at different angles by using the distributed ray source and the detector, where the initial projection data includes projection data that is directly obtained by the detector based on the rays emitted from the plurality of ray source points; a first image reconstruction step of obtaining a first CT image using a reconstruction algorithm according to the acquired initial projection data; an image segmentation step of dividing the first CT image into N first sub-images, where N is a positive integer greater than or equal to 1, and a union of the N first sub-images covers the entire first CT image; a first optimization step of optimizing the N first sub-images to obtain N second sub-images; and an image merging step of merging the N second sub-images to obtain a second CT image.

According to some embodiments, the plurality of ray source points include a first-type ray source point and a second-type ray source point, and the first-type ray source point is at least one of the plurality of ray source points; the initial projection data includes first projection data and second projection data, the first projection data is projection data directly obtained based on a ray emitted from the first-type ray source point, and the second projection data is projection data directly obtained based on a ray emitted from the second-type ray source point; and the imaging device is configured to: optimize the N first sub-images with the first projection data as an optimization objective in a process of optimizing the N first sub-images.

According to some embodiments, a frequency of the ray emitted from the first-type ray source point is higher than a frequency of the ray emitted from the second-type ray source point.

According to some embodiments, in the first optimization step, the N first sub-images are optimized using a first neural network model to obtain the N second sub-images, and the first neural network model is pre-trained.

According to some embodiments, the first neural network model is pre-trained by: performing a forward projection on each second sub-image according to the first-type ray source point so as to obtain first forward projection data; determining a difference between the first forward projection data and the first projection data; and adjusting a parameter of the first neural network model according to the difference between the first forward projection data and the first projection data, so as to minimize the difference between the first forward projection data and the first projection data.

According to some embodiments, the plurality of ray source points includes K first-type ray source points, where K is a positive integer greater than or equal to 1; and the initial projection data includes K first projection data $R_j$, the first projection data $R_j$ is projection data directly obtained based on a ray emitted from a $j^{th}$ first-type ray source point, j is a positive integer, and $1 \le j \le K$.

According to some embodiments, the dividing the first CT image into N first sub-images includes: performing a forward projection on the first CT image Q according to the K first-type ray source points so as to obtain K first initial projection data $P_j$, where the first initial projection data $P_j$ is projection data obtained by performing a forward projection on the first CT image Q according to the $j^{th}$ first-type ray source point; and performing a forward projection on each first sub-image $Q_i$ according to the K first-type ray source points so as to obtain K first projection sub-data $P_{i,j}$ where the first projection sub-data $P_{i,j}$ is projection data obtained by performing a forward projection on an $i^{th}$ first sub-image $Q_i$ according to the j first-type ray source point, i is a positive integer, and $1 \le i \le N$, where in a process of dividing the first CT image into N first sub-images, for any first sub-image and any first-type ray source point, the first initial projection data $P_j$ and the first projection sub-data $P_{i,j}$ are consistent in a partial region $U_{i,j}$.

According to some embodiments, the adjusting a parameter of the first neural network model according to the difference between the first forward projection data and the first projection data so as to minimize the difference between the first forward projection data and the first projection data includes:

for each first sub-image $Q_i$, using a first optimization objective function to minimize the difference between the first forward projection data and the first projection data, where the first optimization objective function is $$\min_{Q_i} \operatorname{sum}_j \left( dis\left(R_j, \overline{P_{i,j}}: U_{i,j}\right)\right),$$

and j takes values from 1 to K sequentially.

In the first optimization objection function, $\overline{Q_i}$ represents an output image of the first neural network model when the first sub-image $Q_i$ is input, $\overline{P_{i,j}}$ represents the first forward projection data, $\overline{P_{i,j}}$ represents the projection data obtained by performing a forward projection on the $i^{th}$ second sub-image $\overline{Q_i}$ according to the $j^{th}$ first-type ray source point, and $dis(R_j, \overline{P_{i,j}}: U_{i,j})$ is a metric function for measuring a distance between $R_j$ and $\overline{P_{i,j}}$ in the region $U_{i,j}$.

According to some embodiments, the adjusting a parameter of the first neural network model according to the difference between the first forward projection data and the first projection data so as to minimize the difference between the first forward projection data and the first projection data includes:

for each first sub-image $Q_i$, using a second optimization objective function to minimize the difference between the first forward projection data and the first projection data, where the second optimization objective function is $$\min \operatorname{sum}_i \left(f(\overline{Q}_i)\right),$$

where $$f(\overline{Q}_i) = \operatorname{sum}_j \left( dis\left(R_j, \overline{P_{i,j}}: U_{i,j}\right)\right),$$

and i takes values from i to N sequentially.

According to some embodiments, a same metric function is used for each first-type ray source point; or different metric functions are used for at least two of the K first-type ray source points.

According to some embodiments, the metric function includes at least one of an L1-norm distance and an L2-norm distance.

According to some embodiments, the acquiring initial projection data of the inspected object at different angles by using the distributed ray source and the detector includes: acquiring the initial projection data of the inspected object in a predetermined scanning angle range by using the distributed ray source and the detector.

According to some embodiments, the imaging device is further configured to perform: a forward projection step of performing a forward projection on the second CT image to obtain second forward projection data; and a second optimization step of processing the second forward projection data to obtain optimized projection data.

According to some embodiments, in the second optimization step, the second forward projection data is processed using a second neural network model to obtain the optimized projection data, and the second neural network model is pre-trained.

According to some embodiments, the second forward projection data includes forward projection data obtained by directly performing a forward projection on the second CT image.

According to some embodiments, the imaging device is further configured to perform: a second image reconstruction step of obtaining a third CT image using a reconstruction algorithm based on the optimized projection data.

According to some embodiments, the imaging method is further configured to: determine the obtained third CT image as the first CT image; and iteratively execute the image segmentation step, the first optimization step, the image merging step, the forward projection step, the second optimization step and the second image reconstruction step until an iteration termination condition is met, and determine the third CT image obtained by a last execution of the second image reconstruction step as a final CT image.

According to some embodiments, the iteration termination condition includes: a number of iterations reaching a specified number of iterations; or a difference between third CT images obtained in two adjacent iterations being less than a specified threshold.

In another aspect, an electronic device is provided, including: one or more processors; and a storage device for storing one or more programs, where the one or more programs are configured to, when executed by the one or more processors, cause the one or more processors to implement the imaging method described above.

In another aspect, a computer-readable storage medium having executable instructions therein is provided, and the instructions are configured to, when executed by a processor, cause the processor to implement the imaging method described above.

In another aspect, a computer program product containing a computer program is provided, and the program is configured to, when executed by a processor, implement the imaging method described above.

In embodiments of the present disclosure, a segmentation may be performed on an initially acquired CT image, the sub-images obtained by the segmentation may be optimized separately and then merged into an optimized CT image, so that a higher-quality CT image may be obtained. In addition, a neural network model is used to separately optimize the sub-images obtained by the segmentation, which is helpful to reduce a computational load and improve a processing speed.

BRIEF DESCRIPTION OF THE DRAWINGS

For better understanding of the present disclosure, the present disclosure will be described in detail according to the accompanying drawings.

DETAILED DESCRIPTION OF EMBODIMENTS

Specific embodiments of the present disclosure will be described in detail below. It should be noted that the embodiments described herein are just illustrative, not for limiting the present disclosure. In the following description, many specific details are set forth to provide a thorough understanding of the present disclosure. However, it will be apparent to those ordinary skilled in the art that these specific details are not necessary for implementations of the present disclosure. In other embodiments, in order to avoid confusing the present disclosure, well-known structures, materials or methods are not specifically described.

Throughout the specification, references to "one embodiment," "an embodiment," "one example," or "an example" mean that a specific feature, structure or characteristic described in conjunction with the embodiment or example is contained in at least one embodiment of the present disclosure. Therefore, the phrases "in one embodiment", "in an embodiment", "one example" or "an example" appearing in various places throughout the specification do not necessarily refer to the same embodiment or example. Further, specific features, structures or characteristics may be combined in one or more embodiments or examples in any suitable combination and/or sub-combination. In addition, those ordinary skilled in the art should understand that the term "and/or" as used here includes any and all combinations of one or more related listed items.

The terms used here are just intended to describe specific embodiments and are not intended to limit the present disclosure. The terms "include", "contain", etc. used here indicate a presence of the feature, step, operation and/or component, but do not exclude a presence or addition of one or more other features, steps, operations or components.

All terms used here (including technical and scientific terms) have the meanings commonly understood by those skilled in the art, unless otherwise defined. It should be noted that the terms used here should be interpreted as having a meaning consistent with the context of the specification, and should not be interpreted in an idealized or overly rigid manner.

Figure 1:
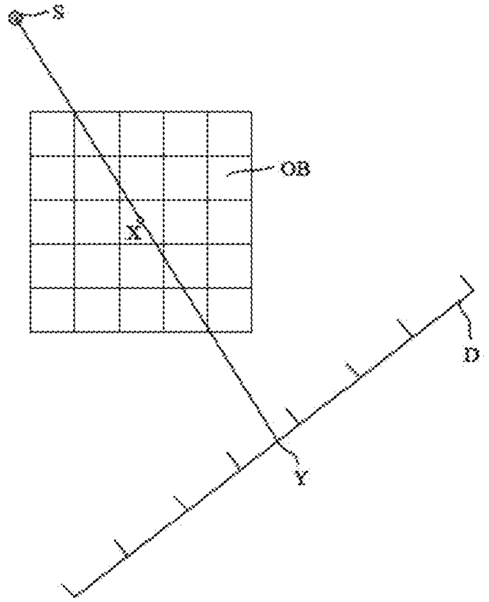
FIG. 1 schematically shows a schematic diagram of a projection relationship between a ray source, an inspected object, and a detector.

FIG. 1 schematically shows a schematic diagram of a projection relationship between a ray source, an inspected object and a detector. Referring to FIG. 1, in embodiments of the present disclosure, rays (such as X-rays, y-rays) emitted from a ray source S are incident on an inspected object OB, and the rays transmitted through the inspected object OB are detected by a detector D. A spatial point X on the inspected object OB is applied to an image point Y on the detector D through the ray source S. In a forward projection, a pixel value of the spatial point on the inspected object OB is known, and a projection value of the image point on the detector D may be calculated. In a backward projection, the projection value of the image point on the detector D is known, and the pixel value of the spatial point on the inspected object OB may be calculated.

Computed Tomography (CT) technology may eliminate an impact of an object overlap, and has played an important role in fields of security inspection, medical care, etc. A conventional CT apparatus may acquire projection data at different angles through a rotation of the X-ray source and the detector by using a slip ring device, and obtain a tomographic image by a reconstruction method, so as to obtain an internal information of a detected luggage item. The conventional CT apparatus generally adopts a slip ring rotation in a data acquisition process, which has a limited scanning speed and a large volume, and requires a high machining accuracy and high costs, so that an application of the CT apparatus in practice is limited. In recent years, a carbon nanotube X-ray tube technology has entered practical fields. Unlike conventional ray sources, it does not need a high temperature to generate rays, but instead generates cathode rays according to a principle of carbon nanotube point discharge and generates X-rays by targeting. It has advantages of quick opening and closing and a smaller volume. By arranging such X-ray sources in a ring shape and irradiating an object at different angles, it is possible to make a static CT apparatus without rotation, which may greatly improve a speed of X-ray imaging. Meanwhile, since the slip ring structure is omitted, the costs may be saved, which is of great significance for fields of security inspection and the like.

Figure 2A:
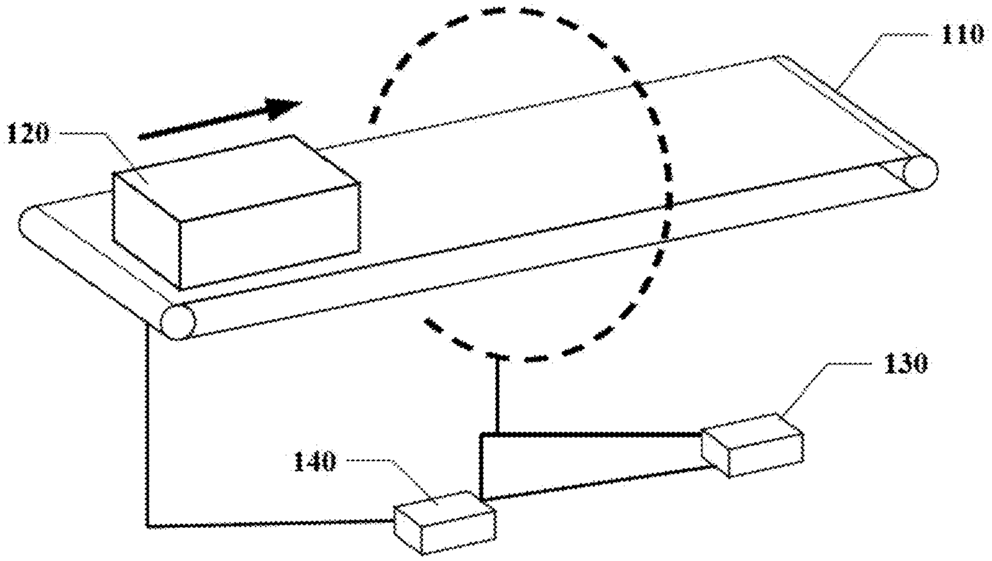
FIG. 2A shows a schematic structural diagram of a static CT apparatus according to some exemplary embodiments of the present disclosure.

FIG. 2A shows a schematic structural diagram of a static CT apparatus according to some exemplary embodiments of the present disclosure. Referring to FIG. 2A, the static CT apparatus according to embodiments of the present disclosure may include a scanning stage, a conveying mechanism 110, a control device 140, and an imaging device 130. For example, the scanning stage may include a ray source, a detector, and an acquisition device.

Figure 2B:
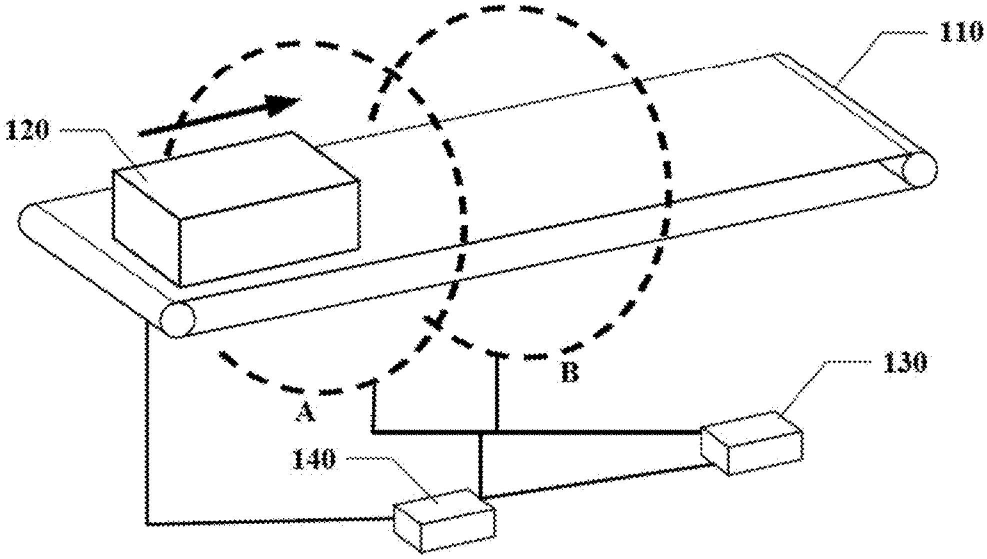
FIG. 2B shows a schematic structural diagram of a static CT apparatus according to other exemplary embodiments of the present disclosure.

FIG. 2B shows a schematic structural diagram of a static CT apparatus according to other exemplary embodiments of the present disclosure. Referring to FIG. 2B, the static CT apparatus according to embodiments of the present disclosure may include a plurality of scanning stages (e.g., a first scanning stage A, a second scanning stage B, . . . ), a conveying mechanism 110, a control device 140, and an imaging device 130. For example, the scanning stage may include a ray source, a detector, and an acquisition device.

For example, in embodiments of the present disclosure, the ray source may be a distributed ray source, which may include a plurality of ray source points, such as a plurality of X-ray source points. For example, each ray source point may be specifically a carbon nanotube X-ray tube.

Figure 3A:
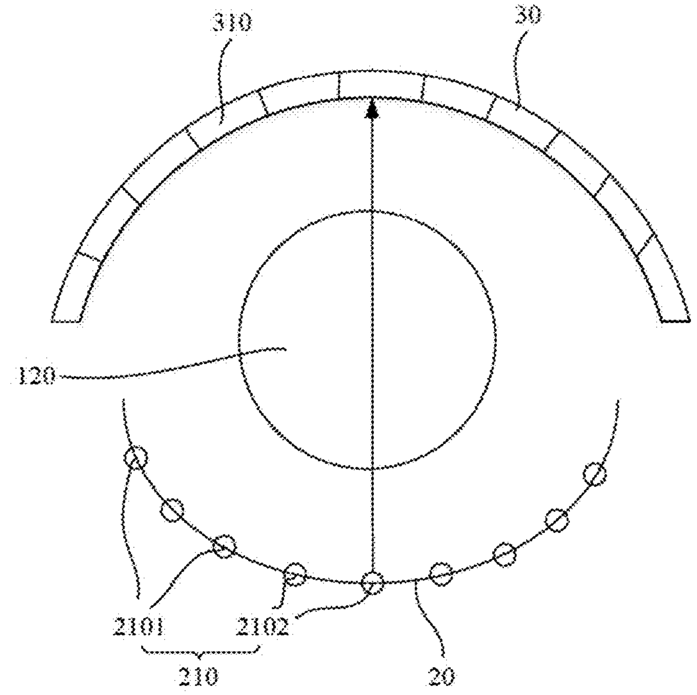
FIG. 3A shows a schematic structural diagram of a scanning stage included in a static CT apparatus according to some exemplary embodiments of the present disclosure.
Figure 3B:
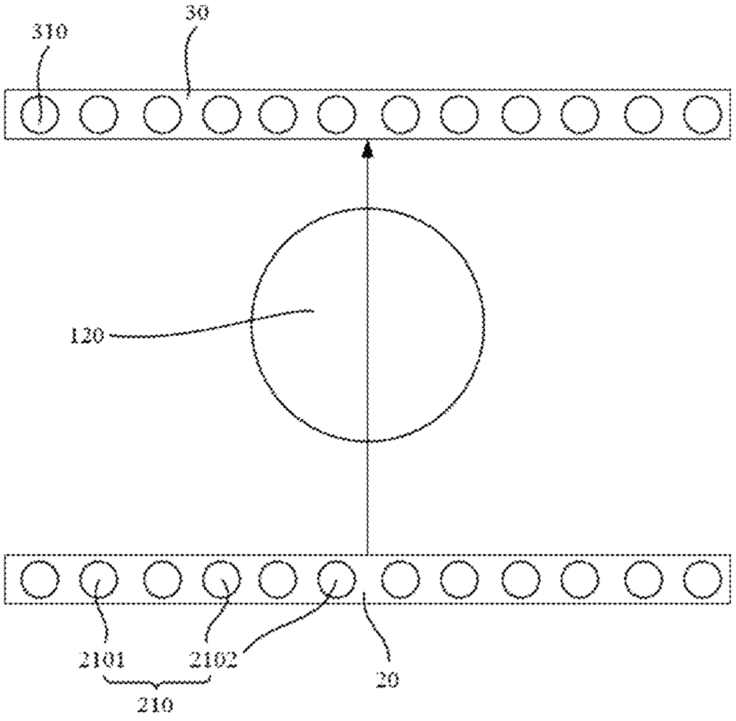
FIG. 3B shows a schematic structural diagram of a scanning stage included in a static CT apparatus according to other exemplary embodiments of the present disclosure.

FIG. 3A shows a schematic structural diagram of a scanning stage included in a static CT apparatus according to some exemplary embodiments of the present disclosure. FIG. 38 shows a schematic structural diagram of a scanning stage included in a static CT apparatus according to other exemplary embodiments of the present disclosure. Referring to FIG. 3A and FIG. 3B, in embodiments of the present disclosure, the static CT apparatus includes a distributed ray source 20 and a detector 30, and the distributed ray source 20 may include a plurality of ray source points 210. In some embodiments, as shown in FIG. 3A, the plurality of ray source points 210 may be arranged in an arc shape. Accordingly, the detector 30 may include a plurality of detection units 310 arranged in an arc or circular shape. In some embodiments, as shown in FIG. 3B, the plurality of ray source points 210 may be arranged along a straight line. Accordingly, the detector 30 may include a plurality of detection units 310 arranged along a straight line. It should be noted that in the embodiments of FIG. 2A to FIG. 3B, only schematic structural diagrams of the static CT apparatus according to some exemplary embodiments of the present disclosure rather than all embodiments of the present disclosure are shown. In embodiments of the present disclosure, any suitable arrangement of the distributed ray source and the detector may be adopted.

In embodiments of the present disclosure, the plurality of ray source points 210 may respectively emit rays towards the inspected object 120, and the plurality of detection units 310 are used to detect the rays passing through the inspected object 120.

For example, in an embodiment shown in FIG. 2A, the conveying mechanism 110 carries the inspected object 120 and drives the inspected object 120 to move along a straight line. The control device 140 may control a beam output order of the plurality of ray source points 210 of the ray source 20, so that the detector 30 outputs a digital signal corresponding to the projection data. The imaging device 130 may reconstruct a CT image of the inspected object 120 based on the digital signal.

It should be noted that in embodiments of the present disclosure, the imaging device 130 may use various known reconstruction algorithms to reconstruct the CT image of the inspected object. For example, the reconstruction algorithm may be an iterative algorithm, an analytical algorithm, or other reconstruction algorithms. The reconstruction algorithm is not specifically limited in embodiments of the present disclosure.

For example, in an embodiment shown in FIG. 2B, the conveying mechanism 110 may carry the inspected object 120 and drive the inspected object 120 to move along a straight line. The first scanning stage A includes a plurality of segments of ray sources, a plurality of segments of detectors, and a first data acquisition device. The first scanning stage A may scan the inspected object to generate a first digital signal. Each of the plurality of segments of ray sources includes a plurality of source points. The second scanning stage B is provided at a predetermined distance from the first scanning stage in a movement direction of the inspected object. The second scanning stage B includes a plurality of segments of ray sources, a plurality of segments of detectors, and a second data acquisition device. The second scanning stage B may scan the inspected object and generate a second digital signal. Each of the plurality of segments of ray sources includes a plurality of source points.

The control device 140 may control a beam output order of the source points in the first scanning stage and the second scanning stage, so that the first scanning stage generates the first digital signal, and the second scanning stage outputs the second digital signal. The imaging device 130 may reconstruct a CT image of the inspected object based on the first digital signal and the second digital signal.

In some embodiments of the present disclosure, each distributed ray source 20 has one or more source points, the energy of the source points may be set, and an order of activating the source points may be set. For example, the source points may be distributed on a plurality of scanning planes (for example, the scanning plane is perpendicular to a channel advancing direction). On each plane, a distribution of the source points may be one or more continuous or discontinuous straight line segments or arc segments. Since the energy of the source point may be set, it is possible to achieve different energy spectra for different source points, or different source point energy for different planes, or other various scanning manners in a beam output process. The source points may be grouped and designed. For example, the source points in each module may be grouped together, or the source points on each plane may be grouped together. An order of electron targeting of the source points in a same group may be adjusted to achieve a sequential beam output or an alternating beam output. The source points in different groups may be activated simultaneously for scanning, so as to increase a scanning speed.

Each scanning stage includes a complete array X-ray detector, a readout circuit, a trigger signal acquisition circuit, and a data transmission circuit. Since the ray source is distributed on a plurality of planes, each plane is provided with a corresponding detector. The detector is arranged in a circular or arc shape. A central column of the detector may be coplanar with the ray source (when the source points are concentrated in a section of a circumference, the detector may be arranged in a remaining section of the circumference), or parallel to the plane where the ray source is located (when the source points are scattered around the circumference, there is no remaining space on the circumference). In order to reduce a slant effect caused by the fact that the ray source and the source point are not located on the same plane, it is required to minimize a distance between the plane where the ray source is located and the plane where the detector is located. The detectors may be positioned in a single row or multiple rows, and a detector type may be single energy, dual energy, or spectral type detector.

The conveying mechanism 110 includes a loading platform or a transport belt. The control device 140 may control an X-ray machine and a frame of the detector. By controlling a beam output mode of the distributed ray source and a linear translation movement of the object or a combination of the two, it is possible to scan with a spiral scanning trajectory, a circumferential scanning trajectory, or other special trajectories. The control device 140 is responsible for controlling an operation process of a CT system, including a mechanical rotation, an electrical control, a safety interlock control, especially for controlling a beam output speed/frequency, a beam energy and a beam sequence of the ray source, and controlling data readout and data reconstruction of the detector.

Figure 4:
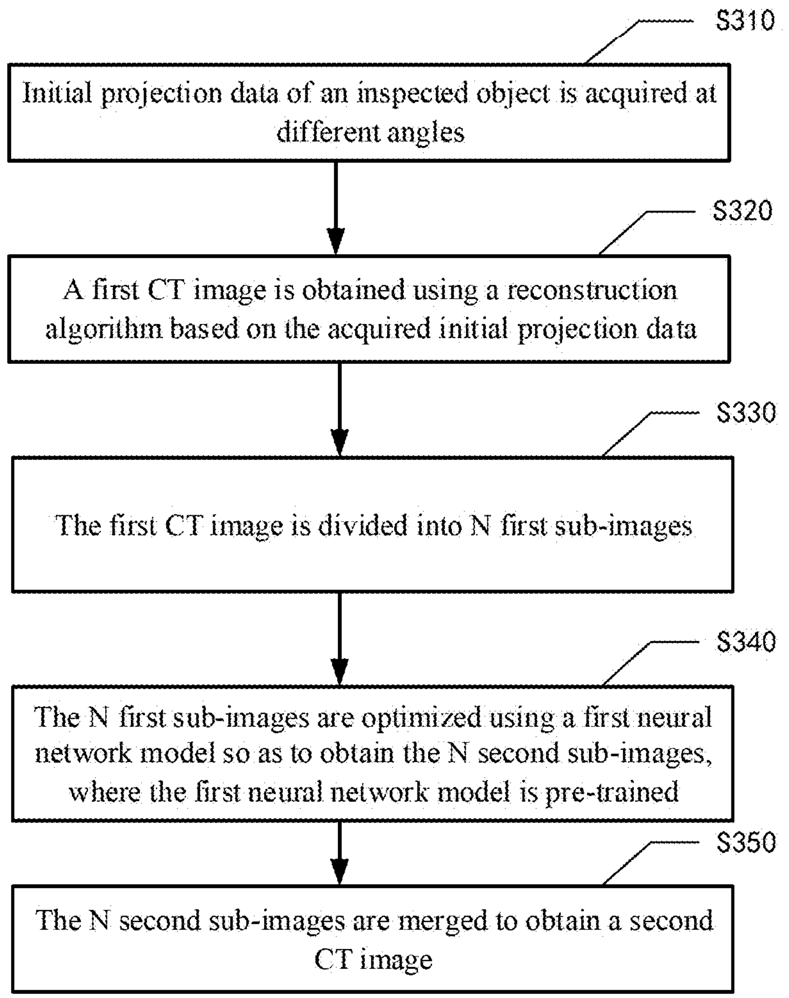
FIG. 4 shows a flowchart of an imaging method for a static CT apparatus according to embodiments of the present disclosure.

FIG. 4 shows a flowchart of an imaging method for a static CT apparatus according to embodiments of the present disclosure. Referring to FIG. 4, the imaging method for the static CT apparatus according to embodiments of the present disclosure may include steps S310 to S350.

It should be noted that in embodiments of the present disclosure, unless otherwise specified, the steps of the imaging method are not limited to be executed in the order described below, and may be executed in parallel or in other orders.

In step S310, an initial projection data acquisition step is performed. For example, in step S310, initial projection data of the inspected object 120 is acquired at different angles by using the distributed ray source 20 and the detector 30. The initial projection data includes projection data that is directly obtained by the detector 30 based on the rays emitted from the plurality of ray source points 210.

In step S320, a first image reconstruction step is performed. For example, in step S320, a first CT image is obtained using a reconstruction algorithm based on the acquired initial projection data.

Figure 5:
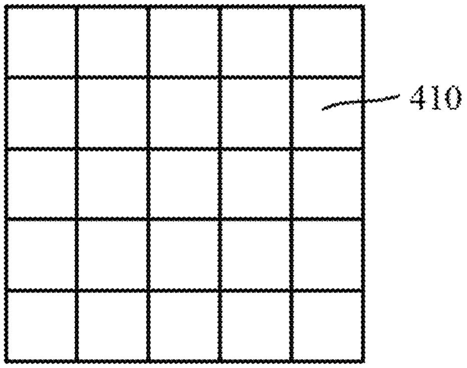
FIG. 5 shows a schematic diagram of a CT image.

In step S330, an image segmentation step is performed. For example, in step S330, the first CT image is divided into N first sub-images, where N is a positive integer greater than or equal to 1, and a union of the N first sub-images covers the entire first CT image. FIG. 5 shows a schematic diagram of a CT image. As shown in FIG. 5, a first CT image 400 is divided into N (e.g., 25) first sub-images 410. Any two of the N first sub-images 410 may partially overlap or not overlap with each other. The union of the N first sub-images 410 covers the entire first CT image 400.

In step S340, a first optimization step is performed. For example, in step S340, the N first sub-images may be optimized to obtain N second sub-images.

For example, in some exemplary embodiments of the present disclosure, in step S340, the N first sub-images are optimized using a first neural network model so as to obtain the N second sub-images, where the first neural network model is pre-trained.

It should be noted that a specific structure of the neural network model is not specifically limited in embodiments of the present disclosure. Without conflict, various known neural network models suitable for image processing may be applicable to embodiments of the present disclosure. For example, the neural network model may include but not be limited to a convolutional neural network model. It should be understood that in the first optimization step, various known machine learning models may be used, which are not limited to a neural network model. For example, in the first optimization step, various machine learning models suitable for image processing may be used, which may include but not be limited to an unsupervised machine learning model based on image segmentation, a supervised machine learning model based on image classification, etc.

In step S350, an image merging step is performed. For example, in step S350, the N second sub-images are merged to obtain a second CT image. It should be understood that the "merging" operation here is an inverse operation of the "segmentation" operation mentioned above.

For example, the second CT image may have a same image size as the first CT image.

In embodiments of the present disclosure, a segmentation is performed on the initially acquired CT image, and the sub-images obtained by the segmentation are optimized separately and then merged into an optimized CT image, so that a higher-quality CT image may be obtained. In addition, a machine learning model such as a neural network model is used to separately optimize the sub-images obtained by the segmentation, which is helpful to reduce a computational load and improve a processing speed.

In embodiments of the present disclosure, the plurality of ray source points 210 include a first-type ray source point and a second-type ray source point, and the first-type ray source point is at least one of the plurality of ray source points. For example, referring to FIG. 3A and FIG. 3B, the plurality of ray source points 210 include a first-type ray source point 2101 and a second-type ray source point 2102. For example, a ratio of the number of the first-type ray source point 2101 to the number of the plurality of ray source points 210 may be below 20%, or below 10%, for example, between 5% and 10%.

In embodiments of the present disclosure, the first-type ray source point 2101 and the second-type ray source point 2102 may be alternately arranged, or the first-type ray source point 2101 and the second-type ray source point 2102 may be arranged in a specified order, which is not specially limited in embodiments of the present disclosure.

In embodiments of the present disclosure, the initial projection data includes first projection data and second projection data. The first projection data is projection data directly obtained based on the ray emitted from the first-type ray source point 2101, and the second projection data is projection data directly obtained based on the ray emitted from the second-type ray source point 2102.

In embodiments of the present disclosure, in a process of optimizing the N first sub-images, such as a process of optimizing the N first sub-images using the first neural network model, the N first sub-images may be optimized with the first projection data as an optimization objective.

For example, the first projection data is projection data that may be used to generate a DR (digital radiography) image. In embodiments of the present disclosure, since the distributed ray source points may be separately controlled for triggering, the DR image may be generated using some ray source points in the distributed ray source and the detector while the CT imaging is performed. The projection data used to generate the CT image and the projection data used to generate the DR image are completely synchronous. With a high resolution of the DR image and a high synchronization of the DR image with the CT image, an imaging quality of the CT image may be improved using the neural network.

For example, a frequency of the ray emitted from the first-type ray source point 2101 is higher than a frequency of the ray emitted from the second-type ray source point 2102.

In embodiments of the present disclosure, the plurality of ray source points include K first-type ray source points, where K is a positive integer greater than or equal to 1.

In embodiments of the present disclosure, since each ray source point in the distributed ray source may be separately controlled for triggering, it is possible to preset a beam output rule for the ray source points to configure the beam output order and beam output frequency of the ray source points. For example, K ($K \geq 1$) ray source points with beam frequency higher than other ray source points may be selected, which is referred to as high-frequency ray source points. Detector readings obtained when all ray source points emit beams are uploaded by an acquisition module of the imaging device and imaged by the imaging device. The high-frequency ray source points emit beams at approximately equal intervals along a time axis. As the inspected object moves with the conveying device, the high-frequency ray source points may generate K perspective images. Due to the high frequency of beam output, these perspective images may directly reflect a structural information of the inspected object. The projection data of all ray source points obtained by the acquisition module may be used to reconstruct the CT image, and the projection data of the high-frequency ray source points is a part of the CT projection data. Therefore, the K perspective images generated by the high-frequency ray source points and the CT image may be unified into a same coordinate system. In such coordinate system, a forward projection is performed on the CT reconstructed image according to the K high-frequency ray source points, then a re-projection image with a structure similar to the DR image may be obtained. An image difference mainly comes from a difference between the reconstructed image and a real image.

The initial projection data includes K first projection data $R_j$. The first projection data $R_j$ is projection data directly obtained based on a ray emitted from a $j^{th}$ first-type ray source point, where j is a positive integer, and $1 \leq j \leq K$.

In embodiments of the present disclosure, dividing the first CT image into N first sub-images may include: performing a forward projection on the first CT image Q according to the K first-type ray source points to obtain K first initial projection data $P_j$, where the first initial projection data $P_j$ is obtained by performing a forward projection on the first CT image Q according to the $j^{th}$ first-type ray source point; and performing a forward projection on each first sub-image $Q_i$ according to the K first-type ray source points to obtain K first projection sub-data $P_{i,j}$ where the first projection sub-data $P_{i,j}$ is obtained by performing a forward projection on an $i^{th}$ first sub-image $Q_i$ according to the $j^{th}$ first-type ray source point, where i is a positive integer, and $1 \leq i \leq N$.

Figure 6:
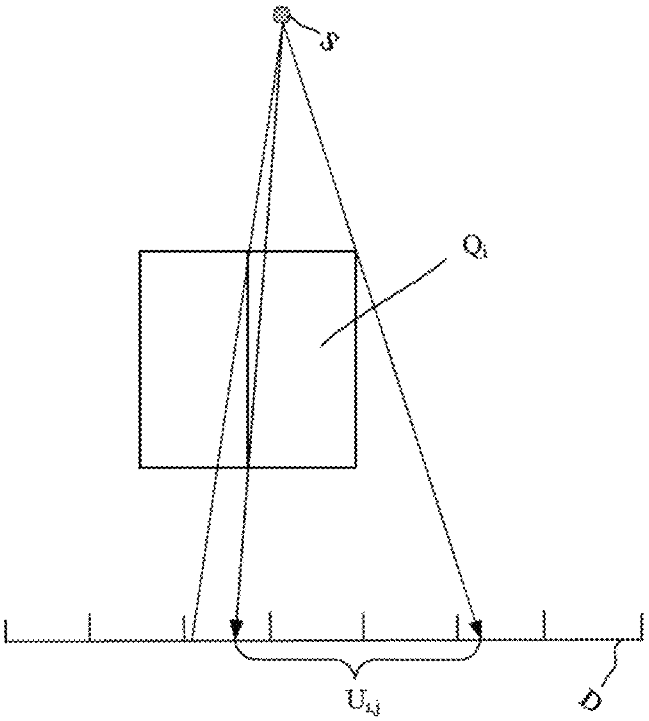
FIG. 6 schematically shows an overlap relationship between first initial projection data and first projection sub-data in a partial region.

FIG. 6 schematically shows an overlap relationship between the first initial projection data and the first projection sub-data in a partial region. Referring to FIG. 6, it should be understood that in the process of dividing the first CI image into N first sub-images, for any first sub-image and any first-type ray source point, the first initial projection data $P_j$ and the first projection sub-data $P_{i,j}$ are consistent in a partial region $U_{i,j}$.

Figure 7:
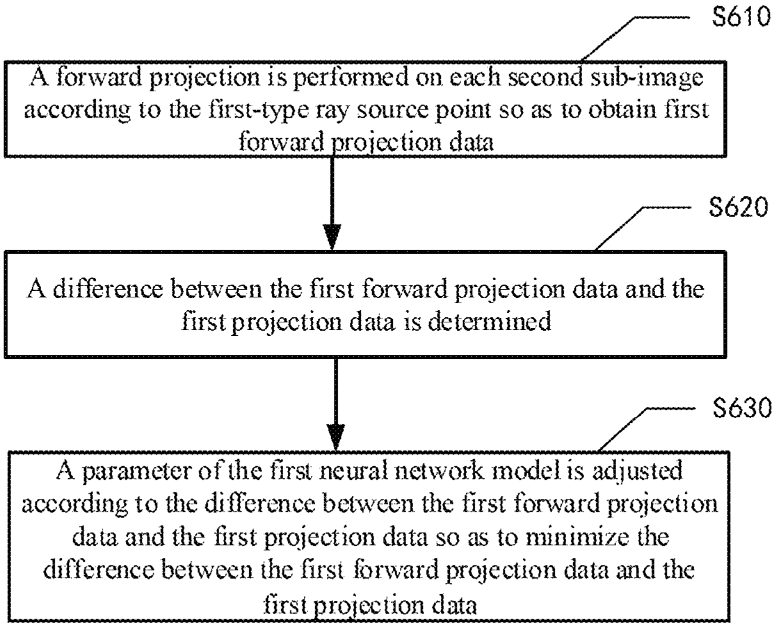
FIG. 7 shows a flowchart of a method of training a first neural network model according to embodiments of the present disclosure.

FIG. 7 shows a flowchart of a method of training a first neural network model according to embodiments of the present disclosure. Referring to FIG. 7, in embodiments of the present disclosure, pre-training the first neural network model may include steps S610 to S630.

In step S610, a forward projection is performed on each second sub-image according to the first-type ray source point so as to obtain first forward projection data.

In step S620, a difference between the first forward projection data and the first projection data is determined.

In step S630, a parameter of the first neural network model is adjusted according to the difference between the first forward projection data and the first projection data so as to minimize the difference between the first forward projection data and the first projection data.

For example, step S630 may include: for each first sub-image $Q_i$, using a first optimization objective function to minimize the difference between the first forward projection data and the first projection data.

For example, the first optimization objective function is $$\min_{Q_i} \operatorname{sum}_j \left( dis\left(R_j, \overline{P_{i,j}}: U_{i,j}\right)\right),$$

where j takes values from 1 to K sequentially.

In the first optimization objection function, $\overline{Q_i}$ represents an output image of the first neural network model when the first sub-image $Q_i$ is input, $\overline{P_{i,j}}$ represents the first forward projection data, $\overline{P_{i,j}}$ represents the projection data that is obtained by performing a forward projection on the $i^{th}$ second sub-image $\overline{Q_i}$ according to the $j^{th}$ first-type ray source point, and dis($R_j$, $\overline{P_{i,j}}$: $U_{i,j}$) is a metric function for measuring a distance between $R_j$ and $\overline{P_{i,j}}$ in the region $U_{i,j}$.

For example, step S630 may include: for each first sub-image $Q_i$, using a second optimization objective function to minimize the difference between the first forward projection data and the first projection data.

The second optimization objective function is min sum(f( $\overline{Q_i}$)), where $$f(\overline{Q_i}) = \operatorname{sum}_j \left( dis\left(R_j, \overline{P_{i,j}}: U_{i,j}\right)\right),$$

and i takes values from i to N sequentially.

In embodiments of the present disclosure, a same metric function is used for each first-type ray source point; or different metric functions are used for at least two of the K first-type ray source points.

For example, the metric function includes at least one of an L1-norm distance and an L2-norm distance.

In embodiments of the present disclosure, acquiring the initial projection data of the inspected object at different angles by using the distributed ray source and the detector may include: acquiring the initial projection data of the inspected object in a predetermined scanning angle range by using the distributed my source and the detector.

Figure 8:
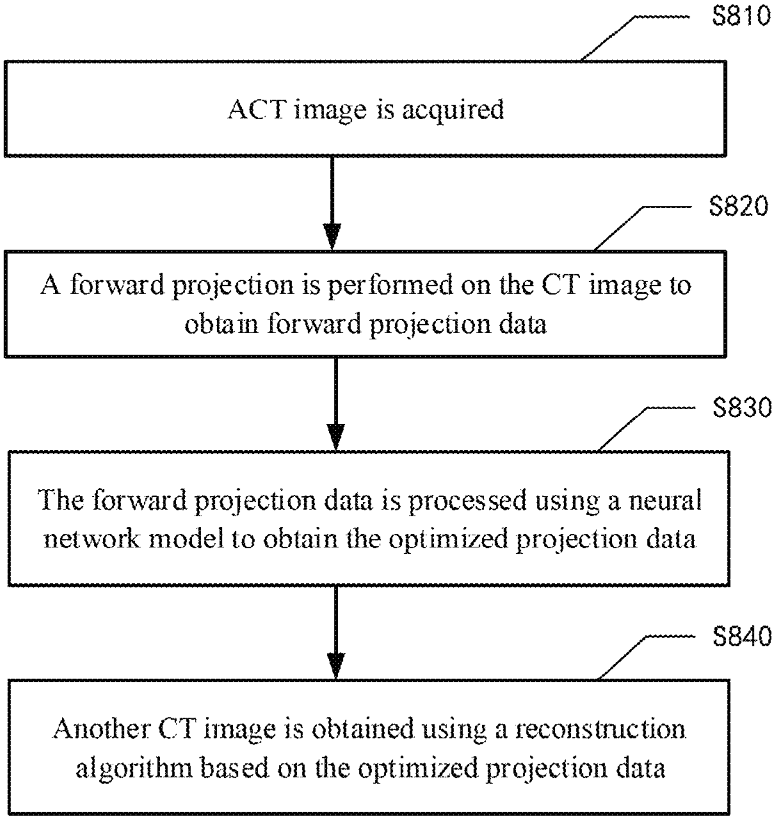
FIG. 8 shows a flowchart of an imaging method for a static CT apparatus according to embodiments of the present disclosure.

FIG. 8 shows a flowchart of an imaging method for a static CT apparatus according to embodiments of the present disclosure. The imaging method may include steps S810 to S840.

In step S810, a CT image acquisition step is performed. For example, in step S810, a CT image is acquired.

In step S820, a forward projection step is performed. For example, in step S820, a forward projection is performed on the CT image to obtain forward projection data.

In step S830, a second optimization step is performed. For example, in step S830, the forward projection data may be processed to obtain optimized projection data.

For example, in some exemplary embodiments of the present disclosure, in step S830, the forward projection data is processed using a neural network model to obtain the optimized projection data, where the neural network model is pre-trained. In order to distinguish the neural network model mentioned here from the neural network model mentioned earlier, the neural network model mentioned here may be referred to as a second neural network model. It should be noted that a specific structure of the neural network model is not specifically limited in embodiments of the present disclosure. Without conflict, various known neural network models suitable for image processing may be applicable to embodiments of the present disclosure. For example, the second neural network model may include but not be limited to a convolutional neural network model. It should be understood that in the second optimization step, various known machine learning models may be used, which are not limited to a neural network model. For example, in the second optimization step, various machine learning models suitable for image processing may be used, which may include but not be limited to a machine learning model based on image segmentation, a data completion model based on compressive sensing, etc.

In step S840, a first image reconstruction step is performed. For example, in step S840, another CT image is obtained using a reconstruction algorithm based on the optimized projection data.

In embodiments of the present disclosure, the CT image obtained in step S810 may be an initial CT image reconstructed based on the initial projection data.

In embodiments of the present disclosure, the above steps may be iteratively executed. For example, the imaging method may include: determining the obtained second CT image as the first CT image; iteratively executing the forward projection step, the first optimization step and the first image reconstruction step until an iteration termination condition is met, and determining the second CT image obtained by a last execution of the first image reconstruction step as a final CT image.

For example, the iteration termination condition may include: a number of the iterations reaching a specified number of iterations; or a difference between the second CT images obtained in two adjacent iterations being less than a specified threshold.

In embodiments of the present disclosure, the CT image obtained in step S810 may be a CT image obtained after an optimization by the first neural network model. That is to say, in the imaging method provided in embodiments of the present disclosure, the optimization by the first neural network model and the optimization by the second neural network model may be used in combination. The optimization by the first neural network model may improve the resolution of the CT image. By inputting the high-resolution CT image to the second neural network model, it is possible to further improve the quality of the finally generated CT image, which is helpful to generate a high-quality CT image.

Figure 9A:
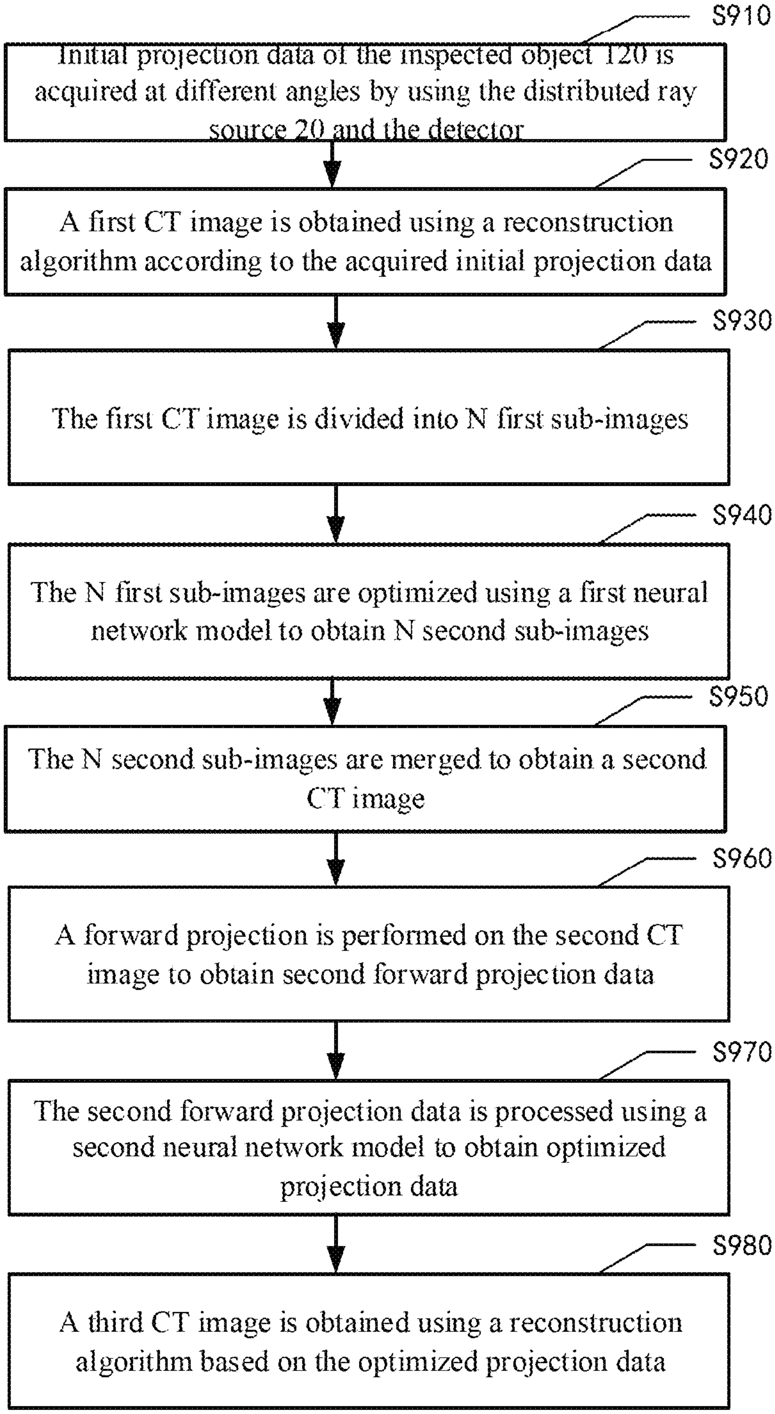
FIG. 9A shows a flowchart of an imaging method for a static CT apparatus according to embodiments of the present disclosure, in which a first neural network model and a second neural network model are used in combination.

FIG. 9A shows a flowchart of an imaging method for a static CT apparatus according to embodiments of the present disclosure, in which a first neural network model and a second neural network model are used in combination. Referring to FIG. 9A, the imaging method for the static CT apparatus according to embodiments of the present disclosure may include steps S910 to S980.

In step S910, an initial projection data acquisition step is performed. For example, in step S910, initial projection data of the inspected object 120 is acquired at different angles by using the distributed ray source 20 and the detector 30. The initial projection data includes projection data that is directly obtained by the detector 30 based on the rays emitted from the plurality of ray source points 210.

In step S920, a first image reconstruction step is performed. For example, in step S920, a first CT image is obtained using a reconstruction algorithm according to the acquired initial projection data.

In step S930, an image segmentation step is performed. For example, in step S930, the first CT image is divided into N first sub-images, where N is a positive integer greater than or equal to 1, and a union of the N first sub-images covers the entire first CT image.

In step S940, a first optimization step is performed. For example, in step S940, the N first sub-images are optimized using a first neural network model to obtain N second sub-images, where the first neural network model is pre-trained.

In step S950, an image merging step is performed. For example, in step S950, the N second sub-images are merged to obtain a second CT image. It should be understood that the “merging” operation here is an inverse operation of the “segmentation” operation mentioned above.

In step S960, a forward projection step is performed. For example, in step S960, a forward projection is performed on the second CT image to obtain second forward projection data.

In step S970, a second optimization step is performed. For example, in step S970, the second forward projection data is processed using a second neural network model to obtain optimized projection data, where the second neural network model is pre-trained.

In step S980, a second image reconstruction step is performed. For example, in step S980, a third CT image is obtained using a reconstruction algorithm based on the optimized projection data.

For example, in some embodiments, the first optimization and the second optimization may be iteratively executed until the finally generated CT image meets specified requirements.

Figure 9B:
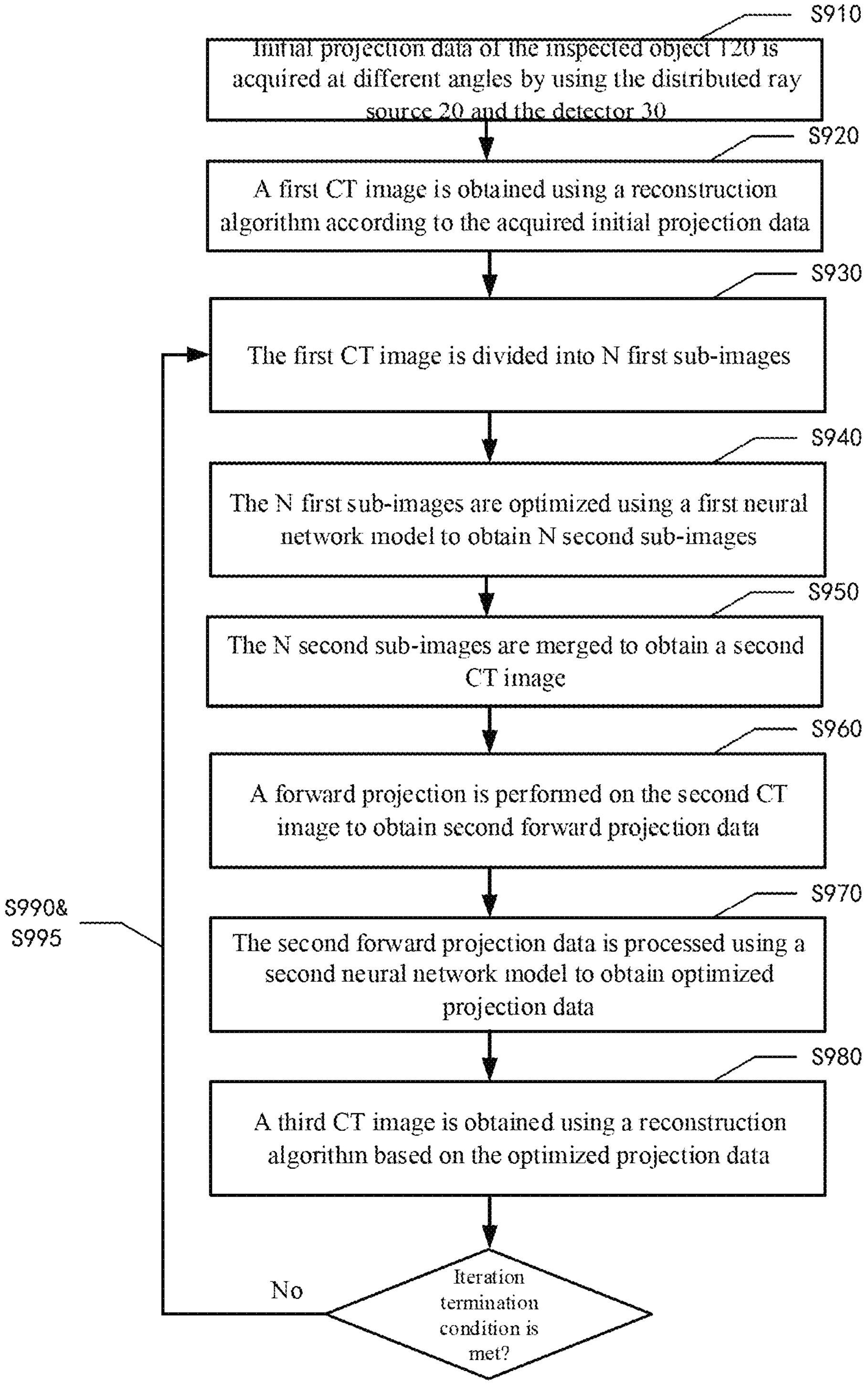
FIG. 9B shows a flowchart of an imaging method for a static CT apparatus according to other embodiments of the present disclosure, in which a first neural network model and a second neural network model are used in combination.

FIG. 9B shows a flowchart of an imaging method for a static CT apparatus according to other embodiments of the present disclosure, in which a first neural network model and a second neural network model are used in combination. Referring to FIG. 9B, in addition to the aforementioned steps S910 to S980, the imaging method for the static CT apparatus according to embodiments of the present disclosure may further include steps S990 to S995.

In step S990, the obtained third CT image is determined as the first CT image.

In step S995, the image segmentation step S930, the first optimization step S940, the image merging step S950, the forward projection step S960, the second optimization step S970 and the second image reconstruction step S990 are iteratively executed until the iteration termination condition is met, and the third CT image obtained by the last execution of the second image reconstruction step is determined as the final CT image.

For example, the iteration termination condition may include: a number of the iterations reaching a specified number of iterations, or a difference between third CT images obtained in two adjacent iterations being less than a specified threshold.

Figure 10:
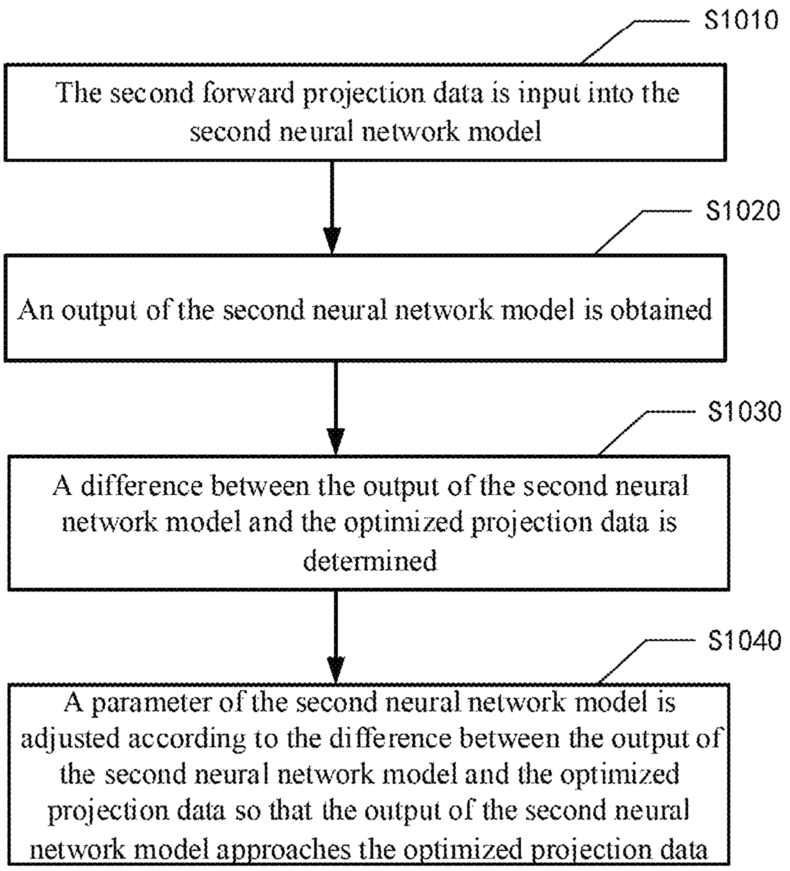
FIG. 10 shows a flowchart of a method of training a second neural network model according to embodiments of the present disclosure.

FIG. 10 shows a flowchart of a method of training a second neural network model according to embodiments of the present disclosure. Referring to FIG. 10, in embodiments of the present disclosure, pre-training the second neural network model may include steps S1010 to S1040.

In step S1010, the second forward projection data is input into the second neural network model.

In step S1020, an output of the second neural network model is obtained.

In step S1030, a difference between the output of the second neural network model and the optimized projection data is determined.

In step S1040, a parameter of the second neural network model is adjusted according to the difference between the output of the second neural network model and the optimized projection data, so that the output of the second neural network model approaches the optimized projection data.

Referring back to FIG. 2A to FIG. 3B, embodiments of the present disclosure further provide a static CT apparatus. The static CT apparatus includes: a distributed ray source 20 including a plurality of ray source points configured to emit rays towards an inspected object; a detector 30 including a plurality of detector units configured to detect the rays passing through the inspected object; an imaging device 130 configured to perform the following steps: an initial projection data acquisition step of acquiring initial projection data of the inspected object at different angles by using the distributed ray source and the detector, where the initial projection data includes projection data directly obtained by the detector based on the rays emitted from the plurality of ray source points, a first image reconstruction step of obtaining a first CT image using a reconstruction algorithm according to the acquired initial projection data; an image segmentation step of dividing the first CT image into N first sub-images, where N is a positive integer greater than or equal to 1, and a union of the N first sub-images covers the entire first CT image; a first optimization step of optimizing the N first sub-images using a first neural network model so as to obtain N second sub-images, where the first neural network model is pre-trained; and an image merging step of merging the N second sub-images to obtain a second CT image.

In embodiments of the present disclosure, the plurality of ray source points 210 include a first-type ray source point 2101 and a second-type ray source point 2102, and the first-type ray source point is at least one of the plurality of ray source points.

The initial projection data includes first projection data and second projection data. The first projection data is projection data directly obtained based on the ray emitted from the first-type ray source point, and the second projection data is projection data directly obtained based on the ray emitted from the second-type ray source point.

The imaging device 130 is configured to optimize the N first sub-images with the first projection data as an optimization objective in a process of optimizing the N first sub-images using the first neural network model.

For example, a frequency of the ray emitted from the first-type ray source point is higher than a frequency of the ray emitted from the second-type ray source point.

In embodiments of the present disclosure, pre-training the first neural network model includes: performing a forward projection on each second sub-image according to the first-type ray source point so as to obtain first forward projection data, determining a difference between the first forward projection data and the first projection data; and adjusting a parameter of the first neural network model according to the difference between the first forward projection data and the first projection data so as to minimize the difference between the first forward projection data and the first projection data.

In embodiments of the present disclosure, acquiring the initial projection data of the inspected object at different angles using the distributed ray source and the detector may include: acquiring the initial projection data of the inspected object in a predetermined scanning angle range using the distributed ray source and the detector.

In embodiments of the present disclosure, the imaging device 130 is further configured to perform the following steps: a forward projection step of performing a forward projection on the second CT image to obtain second forward projection data; and a second optimization step of processing the second forward projection data using a second neural network model so as to obtain optimized projection data, where the second neural network model is pre-trained.

In embodiments of the present disclosure, pre-training the second neural network model includes: inputting the second forward projection data into the second neural network model; obtaining an output of the second neural network model; determining a difference between the output of the second neural network model and the optimized projection data; and adjusting a parameter of the second neural network model according to the difference between the output of the second neural network model and the optimized projection data so that the output of the second neural network model approaches the optimized projection data.

In embodiments of the present disclosure, the imaging device 130 is further configured to perform a second image reconstruction step of, for example, obtaining a third CT image using a reconstruction algorithm based on the optimized projection data.

In embodiments of the present disclosure, the imaging device 130 is further configured to perform the following steps: determining the acquired third CT image as the first CT image; iteratively executing the image segmentation step, the first optimization step, the image merging step, the forward projection step, the second optimization step and the second image reconstruction step until an iteration termination condition is met, and determining the third CT image obtained by the last execution of the second image reconstruction step as the final CT image.

For example, the iteration termination condition may include: a number of the iterations reaching a specified number of iterations; or a difference between third CT images obtained in two adjacent iterations being less than a specified threshold.

Figure 11:
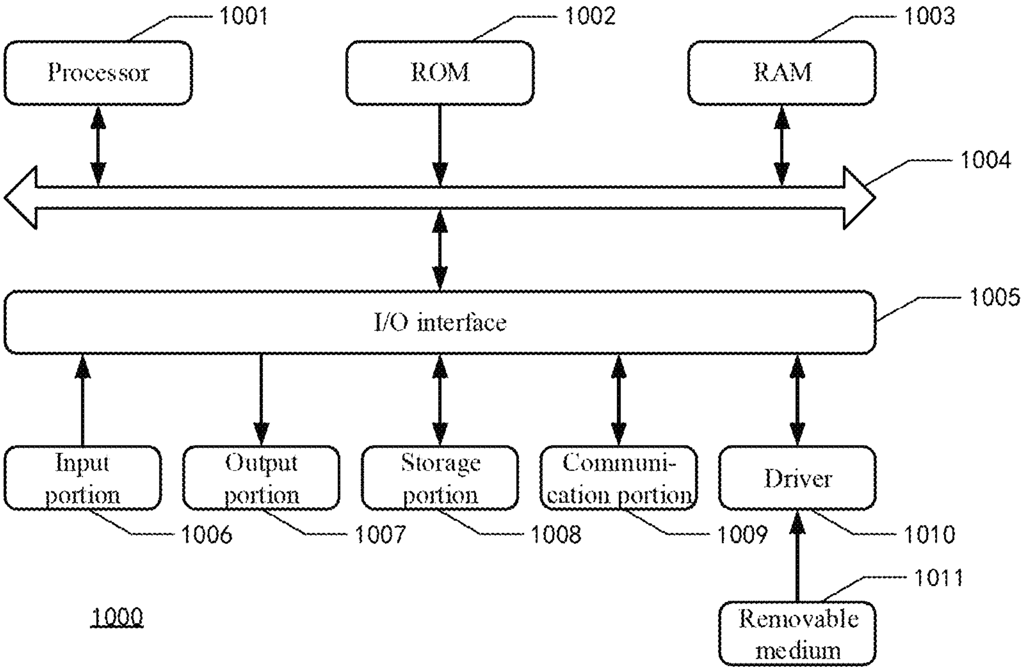
FIG. 11 schematically shows a structural block diagram of an electronic device suitable for the above-mentioned methods according to exemplary embodiments of the present disclosure.

FIG. 11 schematically shows a structural block diagram of an electronic device suitable for the above-mentioned methods according to exemplary embodiments of the present disclosure.

As shown in FIG. 11, an electronic device 1000 according to embodiments of the present disclosure includes a processor 1001, which may execute various appropriate actions and processing according to a program stored in a read only memory (ROM) 1002 or a program loaded into a random access memory (RAM) 1003 from a storage portion 1008. The processor 1001 may include, for example, a general-purpose microprocessor (for example, CPU), an instruction set processor and/or a related chipset and/or a special-purpose microprocessor (for example, an application specific integrated circuit (ASIC)), and the like. The processor 1001 may further include an on-board memory for caching purposes. The processor 1001 may include a single processing unit or a plurality of processing units for executing different actions of the method flow according to embodiments of the present disclosure.

Various programs and data required for operations of the electronic device 1000 are stored in the RAM 1003. The processor 1001, the ROM 1002 and the RAM 1003 are connected to each other through a bus 1004. The processor 1001 executes various operations of the method flow according to embodiments of the present disclosure by executing the programs in the ROM 1002 and/or the RAM 1003. It should be noted that the program may also be stored in one or more memories other than the ROM 1002 and the RAM 1003. The processor 1001 may also execute various operations of the method flow according to embodiments of the present disclosure by executing the programs stored in the one or more memories.

According to embodiments of the present disclosure, the electronic device 1000 may further include an input/output (I/O) interface 1005 which is also connected to the bus 1004. The electronic device 1000 may further include one or more of the following components connected to the/O interface 1005: an input portion 1006 including a keyboard, a mouse, etc.; an output portion 1007 including a cathode ray tube (CRT), a liquid crystal display (LCD), etc. and a speaker, etc.; a storage portion 1008 including a hard disk, etc.; and a communication portion 1009 including a network interface card such as a LAN card, a modem, and the like. The communication portion 1009 performs communication processing via a network such as the Internet. A driver 1010 is also connected to the I/O interface 1005 as required. A removable medium 1011, such as a magnetic disk, an optical disk, a magneto-optical disk, a semiconductor memory, and the like, is installed on the driver 1010 as required, so that the computer program read therefrom is installed into the storage portion 1008 as needed.

The present disclosure further provide a computer-readable storage medium, which may be included in the apparatus/device/system described in the aforementioned embodiments; or exist alone without being assembled into the apparatus/device/system. The computer-readable storage medium carries one or more programs that when executed, perform the method according to embodiments of the present disclosure.

According to embodiments of the present disclosure, the computer-readable storage medium may be a non-transitory computer-readable storage medium, for example, which may include but not be limited to: a portable computer disk, a hard disk, a random access memory (RAM), a read-only memory (ROM), an erasable programmable read-only memory (EPROM or flash memory), a portable compact disk read-only memory (CD-ROM), an optical storage device, a magnetic storage device, or any suitable combination of the above. In the present disclosure, the computer-readable storage medium may be any tangible medium that contains or stores programs that may be used by or in combination with an instruction execution system, apparatus or device. For example, according to embodiments of the present disclosure, the computer-readable storage medium may include the above-mentioned ROM 1002 and/or RAM 1003 and/or one or more memories other than the ROM 1002 and RAM 1003.

Embodiments of the present disclosure further include a computer program product, which contains a computer program. The computer program contains program codes for performing the methods shown in flowcharts. When the computer program product runs on a computer system, the program codes are used to cause the electronic device to implement the method provided in embodiments of the present disclosure.

When the computer program is executed by the processor 1001, the functions defined in the system/apparatus of embodiments of the present disclosure are performed. According to embodiments of the present disclosure, the above-mentioned systems, apparatuses, modules, units, etc. may be implemented by computer program modules.

In an embodiment, the computer program may rely on a tangible storage medium such as an optical storage device and a magnetic storage device. In another embodiment, the computer program may also be transmitted and distributed in the form of signals on a network medium, downloaded and installed through the communication portion 1009, and/or installed from the removable medium 1011. The program codes contained in the computer program may be transmitted by any suitable network medium, including but not limited to a wireless one, a wired one, or any suitable combination of the above.

In such embodiments, the computer program may be downloaded and installed from the network via the communication portion 1009 and/or installed from the removable medium 1011. When the computer program is executed by the processor 1001, the above-mentioned functions defined in the systems of embodiments of the present disclosure are performed. According to embodiments of the present disclosure, the systems, apparatuses, devices, modules, units, etc. described above may be implemented by computer program modules.

According to embodiments of the present disclosure, the program codes for executing the computer programs provided by embodiments of the present disclosure may be written in any combination of one or more programming languages. In particular, these computing programs may be implemented using high-level procedures and/or object-oriented programming languages, and/or assembly/machine languages. Programming languages include, but are not limited to, Java, C++, Python, "C" language or similar programming languages. The program codes may be completely executed on a user computing device, partially executed on a user device, partially executed on a remote computing device, or completely executed on a remote computing device or a server. In a case of involving a remote computing device, the remote computing device may be connected to the user computing device through any kind of network, including local area network (LAN) or wide area network (WAN), or may be connected to an external computing device (e.g., through the Internet using an Internet service provider).

The flowcharts and block diagrams in the accompanying drawings illustrate the possible architecture, functions, and operations of the system, method, and computer program product according to various embodiments of the present disclosure. In this regard, each block in the flowcharts or block diagrams may represent a part of a module, a program segment, or a code, which part includes one or more executable instructions for implementing the specified logical function. It should be further noted that, in some alternative implementations, the functions noted in the blocks may also occur in a different order from that noted in the accompanying drawings. For example, two blocks shown in succession may actually be executed substantially in parallel, or they may sometimes be executed in a reverse order, depending on the functions involved. It should be further noted that each block in the block diagrams or flowcharts, and the combination of blocks in the block diagrams or flowcharts, may be implemented by a dedicated hardware-based system that performs the specified functions or operations, or may be implemented by a combination of dedicated hardware and computer instructions.

Those skilled in the art may understand that the various embodiments of the present disclosure and/or the features described in the claims may be combined in various ways, even if such combinations are not explicitly described in the present disclosure. In particular, without departing from the spirit and teachings of the present disclosure, the various embodiments of the present disclosure and/or the features described in the claims may be combined in various ways. All these combinations fall within the scope of the present disclosure.

Embodiments of the present disclosure have been described above. However, these embodiments are for illustrative purposes only, and are not intended to limit the scope of the present disclosure. Although the various embodiments have been described separately above, this does not mean that measures in the respective embodiments may not be used in combination advantageously. The scope of the present disclosure is defined by the appended claims and their equivalents. Those skilled in the art may make various substitutions and modifications without departing from the scope of the present disclosure, and these substitutions and modifications should all fall within the scope of the present disclosure.

What is claimed is:

1. An imaging method for a static CT apparatus, wherein the static CT apparatus comprises a distributed ray source and a detector, the distributed ray source comprises a plurality of ray source points configured to emit rays towards an inspected object, and the detector comprises a plurality of detector units configured to detect the rays passing through the inspected object, wherein the imaging method comprises:

an initial projection data acquisition step of acquiring initial projection data of the inspected object at different angles by using the distributed ray source and the detector, wherein the initial projection data comprises projection data that is directly obtained by the detector based on the rays emitted from the plurality of ray source points;

a first image reconstruction step of obtaining a first CT image using a reconstruction algorithm according to the acquired initial projection data;

an image segmentation step of dividing the first CT image into N first sub-images, where N is a positive integer greater than or equal to 1, and a union of the N first sub-images covers the entire first CT image;

a first optimization step of optimizing the N first sub-images to obtain N second sub-images; and an image merging step of merging the N second sub-images to obtain a second CT image, wherein the plurality of ray source points comprise a first-type ray source point and a second-type ray source point, and the first-type ray source point is at least one of the plurality of ray source points;

wherein the initial projection data comprises first projection data and second projection data, the first projection data is projection data directly obtained based on a ray emitted from the first-type ray source point, and the second projection data is projection data directly obtained based on a ray emitted from the second-type ray source point; and wherein the N first sub-images are optimized with the first projection data as an optimization objective in a process of optimizing the N first sub-images.

2. The imaging method according to claim 1, wherein a frequency of the ray emitted from the first-type ray source point is higher than a frequency of the ray emitted from the second-type ray source point.

3. The imaging method according to claim 1, wherein in the first optimization step, the N first sub-images are optimized using a first neural network model to obtain the N second sub-images, and the first neural network model is pre-trained.

4. The imaging method according to claim 3, wherein the first neural network model is pre-trained by:

performing a forward projection on each second sub-image according to the first-type ray source point so as to obtain first forward projection data;

determining a difference between the first forward projection data and the first projection data; and adjusting a parameter of the first neural network model according to the difference between the first forward projection data and the first projection data, so as to minimize the difference between the first forward projection data and the first projection data.

5. The imaging method according to claim 1, wherein the plurality of ray source points comprises K first-type ray source points, where K is a positive integer greater than or equal to 1; and wherein the initial projection data comprises K first projection data $R_j$, the first projection data $R_j$ is projection data directly obtained based on a ray emitted from a $j^{th}$ first-type ray source point, j is a positive integer, and $1 \leq j \leq K$.

6. The imaging method according to claim 5, wherein the dividing the first CT image into N first sub-images comprises:

performing a forward projection on the first CT image Q according to the K first-type ray source points so as to obtain K first initial projection data $P_j$, wherein the first initial projection data $P_j$ is projection data obtained by performing a forward projection on the first CT image Q according to the $j^{th}$ first-type ray source point; and performing a forward projection on each first sub-image $Q_i$ according to the K first-type ray source points so as to obtain K first projection sub-data $P_{i,j}$, wherein the first projection sub-data $P_{i,j}$ is projection data obtained by performing a forward projection on an $i^{th}$ first sub-image $Q_i$ according to the $j^{th}$ first-type ray source point, i is a positive integer, and $1 \leq i \leq N$, wherein in a process of dividing the first CT image into N first sub-images, for any first sub-image and any first-type ray source point, the first initial projection data $P_j$ and the first projection sub-data $P_{i,j}$ are consistent in a partial region $U_{i,j}$.

7. The imaging method according to claim 1, wherein the acquiring initial projection data of the inspected object at different angles by using the distributed ray source and the detector comprises:

acquiring the initial projection data of the inspected object in a predetermined scanning angle range by using the distributed ray source and the detector.

8. The imaging method according to claim 7, further comprising:

a forward projection step of performing a forward projection on the second CT image to obtain second forward projection data; and a second optimization step of processing the second forward projection data to obtain optimized projection data.

9. The imaging method according to claim 8, wherein in the second optimization step, the second forward projection data is processed using a second neural network model to obtain the optimized projection data, and the second neural network model is pre-trained.

10. The imaging method according to claim 8, wherein the second forward projection data comprises forward projection data obtained by directly performing a forward projection on the second CT image.

11. The imaging method according to claim 8, further comprising:

a second image reconstruction step of obtaining a third CT image using a reconstruction algorithm based on the optimized projection data.

12. The imaging method according to claim 11, further comprising:

determining the obtained third CT image as the first CT image; and iteratively executing the image segmentation step, the first optimization step, the image merging step, the forward projection step, the second optimization step and the second image reconstruction step until an iteration termination condition is met, and determining the third CT image obtained by a last execution of the second image reconstruction step as a final CT image.

13. The imaging method according to claim 12, wherein the iteration termination condition comprises:

a number of iterations reaching a specified number of iterations; or a difference between third CT images obtained in two adjacent iterations being less than a specified threshold.

14. A static CT apparatus, comprising:

a distributed ray source, wherein the distributed ray source comprises a plurality of ray source points configured to emit rays towards an inspected object;

a detector, wherein the detector comprises a plurality of detector units configured to detect the rays passing through the inspected object; and an imaging device configured to perform:

an initial projection data acquisition step of acquiring initial projection data of the inspected object at different angles by using the distributed ray source and the detector, wherein the initial projection data comprises projection data that is directly obtained by the detector based on the rays emitted from the plurality of ray source points;

a first image reconstruction step of obtaining a first CT image using a reconstruction algorithm according to the acquired initial projection data;

an image segmentation step of dividing the first CT image into N first sub-images, where N is a positive integer greater than or equal to 1, and a union of the N first sub-images covers the entire first CT image;

a first optimization step of optimizing the N first sub-images to obtain N second sub-images; and an image merging step of merging the N second sub-images to obtain a second CT image, wherein the plurality of ray source points comprise a first-type ray source point and a second-type ray source point, and the first-type ray source point is at least one of the plurality of ray source points;

wherein the initial projection data comprises first projection data and second projection data, the first projection data is projection data directly obtained based on a ray emitted from the first-type ray source point, and the second projection data is projection data directly obtained based on a ray emitted from the second-type ray source point; and wherein the imaging device is configured to: optimize the N first sub-images with the first projection data as an optimization objective in a process of optimizing the N first sub-images.

15. The apparatus according to claim 14, wherein a frequency of the ray emitted from the first-type ray source point is higher than a frequency of the ray emitted from the second-type ray source point.

16. The apparatus according to claim 14, wherein in the first optimization step, the N first sub-images are optimized using a first neural network model to obtain the N second sub-images, and the first neural network model is pre-trained.

17. The apparatus according to claim 16, wherein the first neural network model is pre-trained by:

performing a forward projection on each second sub-image according to the first-type ray source point so as to obtain first forward projection data;

determining a difference between the first forward projection data and the first projection data; and adjusting a parameter of the first neural network model according to the difference between the first forward projection data and the first projection data, so as to minimize the difference between the first forward projection data and the first projection data.

18. The apparatus according to claim 14, wherein the plurality of ray source points comprises K first-type ray source points, where K is a positive integer greater than or equal to 1; and wherein the initial projection data comprises K first projection data $R_j$, the first projection data $R_j$ is projection data directly obtained based on a ray emitted from a $j^{th}$ first-type ray source point, j is a positive integer, and $1 \leq j \leq K$.

19. The apparatus according to claim 18, wherein the dividing the first CT image into N first sub-images comprises:

performing a forward projection on the first CT image Q according to the K first-type ray source points so as to obtain K first initial projection data $P_j$, wherein the first initial projection data $P_j$ is projection data obtained by performing a forward projection on the first CT image Q according to the $j^{th}$ first-type ray source point; and performing a forward projection on each first sub-image $Q_i$ according to the K first-type ray source points so as to obtain K first projection sub-data $P_{i,j}$, wherein the first projection sub-data $P_{i,j}$ is projection data obtained by performing a forward projection on an $i^{th}$ first sub-image $Q_i$ according to the $j^{th}$ first-type ray source point, i is a positive integer, and $1 \le i \le N$, wherein in a process of dividing the first CT image into N first sub-images, for any first sub-image and any first-type ray source point, the first initial projection data $P_j$ and the first projection sub-data $P_{i,j}$ are consistent in a partial region $U_{i,j}$.

20. The apparatus according to claim 14, wherein the acquiring initial projection data of the inspected object at different angles by using the distributed ray source and the detector comprises:

acquiring the initial projection data of the inspected object in a predetermined scanning angle range by using the distributed ray source and the detector.

21. The apparatus according to claim 20, wherein the imaging device is further configured to perform:

a forward projection step of performing a forward projection on the second CT image to obtain second forward projection data; and a second optimization step of processing the second forward projection data to obtain optimized projection data.

22. The apparatus according to claim 21, wherein in the second optimization step, the second forward projection data is processed using a second neural network model to obtain the optimized projection data, and the second neural network model is pre-trained.

23. The apparatus according to claim 21, wherein the second forward projection data comprises forward projection data obtained by directly performing a forward projection on the second CT image.

24. The apparatus according to claim 21, wherein the imaging device is further configured to perform:

a second image reconstruction step of obtaining a third CT image using a reconstruction algorithm based on the optimized projection data.

25. The apparatus according to claim 24, wherein the imaging device is further configured to:

determine the obtained third CT image as the first CT image; and iteratively execute the image segmentation step, the first optimization step, the image merging step, the forward projection step, the second optimization step and the second image reconstruction step until an iteration termination condition is met, and determine the third CT image obtained by a last execution of the second image reconstruction step as a final CT image.

26. The apparatus according to claim 25, wherein the iteration termination condition comprises:

a number of iterations reaching a specified number of iterations; or a difference between third CT images obtained in two adjacent iterations being less than a specified threshold.

* * * * *